(12) United States Patent
Zogbi et al.

(10) Patent No.: US 6,656,135 B2
(45) Date of Patent: Dec. 2, 2003

(54) PASSIVE AND WIRELESS DISPLACEMENT MEASURING DEVICE

(75) Inventors: Susan W. Zogbi, San Antonio, TX (US); Larry D. Canady, San Antonio, TX (US); Jerome A. Helffrich, San Antonio, TX (US); Stephen A. Cerwin, Pittsboro, NC (US); Kevin S. Honeyager, San Antonio, TX (US); Armando de los Santos, San Antonio, TX (US); Christopher B. Catterson, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 0 days.

(21) Appl. No.: 09/789,832

(22) Filed: Feb. 20, 2001

(65) Prior Publication Data

US 2002/0147416 A1 Oct. 10, 2002

Related U.S. Application Data

(60) Provisional application No. 60/200,835, filed on May 1, 2000.

(51) Int. Cl.$^7$ ............................................. A61B 5/103
(52) U.S. Cl. ....................... 600/594; 600/587; 600/595; 128/897; 324/207.11
(58) Field of Search ................................. 600/300, 587, 600/594, 595; 128/897–899; 340/573.1; 324/207.11–207.2, 209.24, 236; 33/511, 512; 73/865.1, 865.4

(56) References Cited

U.S. PATENT DOCUMENTS

| | | | |
|---|---|---|---|
| 4,618,822 A | * | 10/1986 | Hansen .................. 324/207.16 |
| 4,816,759 A | * | 3/1989 | Ames et al. ........... 324/207.17 |
| 4,971,069 A | | 11/1990 | Gracovetsky ............... 600/594 |
| 5,143,088 A | | 9/1992 | Marras et al. .............. 600/594 |
| 5,146,929 A | | 9/1992 | Sawhill ...................... 600/594 |
| 5,474,086 A | | 12/1995 | McCormick et al. ....... 600/594 |
| 5,772,610 A | | 6/1998 | McGorry et al. ........... 600/594 |
| 6,245,109 B1 | | 6/2001 | Mendes et al. .......... 623/18.11 |

OTHER PUBLICATIONS

O'Connor, Roy; Bak, David J.; "Six Sensor Systems . . . "; Design News Online; http://www.manufacturing.net/magazine/dn/archives/1999/dn0322.99/feature2.html, Mar. 22, 1999.

Euclid Research; "Motion Sensor Reference"; http://www.euclidres.com/motionSensors/motionSensors.html.

RDP Electronics, Ltd. "Linear Variable Differential Transformer Principle of Operation"; http://www.rdpelectronics.com/displacement/lvdt/lvdt–principles.htm.

G.L. Collins Corporation; "LVDT Principle of Operation"; http://www.lvdtcollins.com/lvdt/lvdt.htm.

Solartron; "Principle of LVDT Operation"; http://www.solartron–metrology.com/lvdt.htm.

Eibeck, Pamela A., Muramatsu, Brandon; "LVDT"; http://bits.me/berkeley.edu/beam/lvdt_1.html.

* cited by examiner

Primary Examiner—Charles Marmor
(74) Attorney, Agent, or Firm—Baker Botts L.L.P.

(57) ABSTRACT

A system that remotely measures displacement between two objects. A passive sensor is affixed between the objects. The internal sensor uses magnetic coupling between two sensor elements to measure their relative displacement. The sensors are either a) a permeable rod and a complimentary coil in parallel with a tuning capacitor; or b) two permeable rods, each having its own surrounding coil and a tuning capacitor. One of the sensor elements is affixed to each object which is to be monitored. When an interrogating device is placed near the sensors, a resonance can be measured whose frequency characteristics change in a reproducible manner with the relative displacement of the sensors. The resulting resonance characteristics can be calibrated in such a way as to enable the displacement of the objects to be determined.

24 Claims, 4 Drawing Sheets

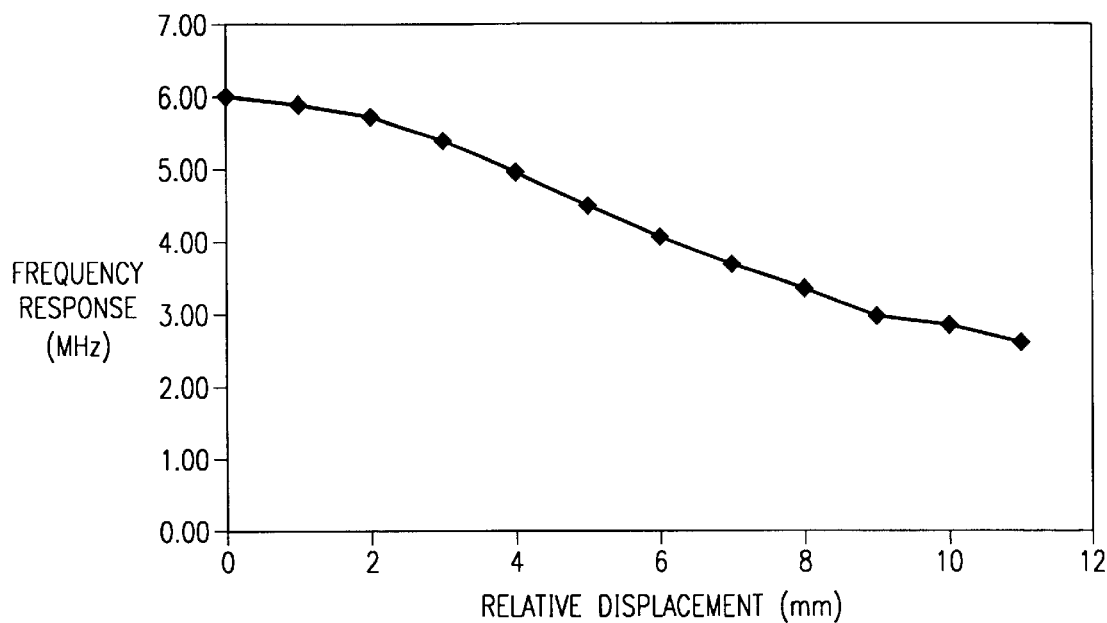
FIG. 9
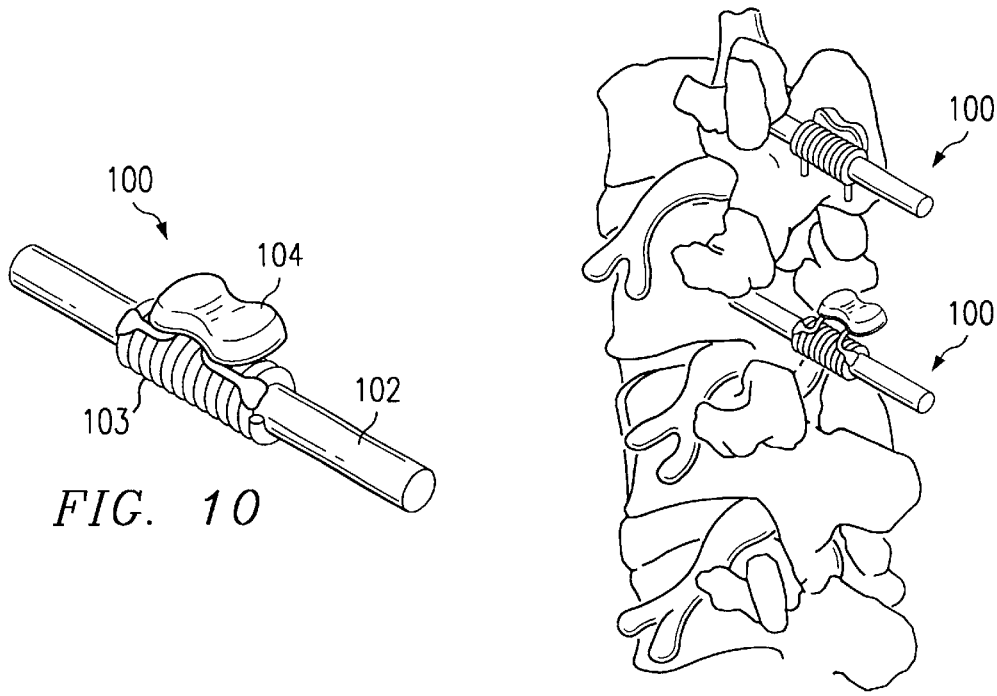
FIG. 10
FIG. 11

PASSIVE AND WIRELESS DISPLACEMENT MEASURING DEVICE

RELATED PATENT APPLICATION

This application claims the benefit of U.S. Provisional Application No. 60/200,835, filed May 1, 2000 and entitled "Passive Spinal Fusion Diagnostic System".

TECHNICAL FIELD OF THE INVENTION

This invention relates to devices for measuring displacement, and more particularly to a wireless device that can be implanted between two adjacent objects and used to measure changes in their separation distance.

BACKGROUND OF THE INVENTION

Displacement and proximity sensors play large roles in the automotive, aerospace, food, beverage, metal, and computer industries. The increase in automation has vastly increased the demand for such sensors. This demand is due to the replacement of outdated plant equipment and the overall increase in factory automation.

Of the sensors in the proximity and displacement sensor market, inductive (magnetic) and photoelectric sensors are probably the most popular. Other types of displacement sensors are capacitive sensors, ultrasonic sensors, potentiometric sensors, laser sensors, and ultrasonic sensors.

Magnetic displacement sensors include LVDT (linear variable differential transform) sensors, hall effect sensors, and magnetostrictive sensors. LVDT sensors use three coils, a primary coil and two secondary coils. The secondary coils are connected to establish a null position. A magnetic core inside the coil winding assembly provides a magnetic flux. When the core is displaced from the null position, an electromagnetic imbalance occurs. Hall effect sensors are based on a voltage that is generated in one direction when a current and a magnetic field pass through semiconductor material in the other two perpendicular directions.

Variations of magnetic and inductive sensors have been developed with one or two coils. A disadvantage of many magnetic and inductive designs is the need for an electrical connection to the sensor.

SUMMARY OF THE INVENTION

One aspect of the invention is a sensor/interrogator system for measuring displacement between two adjacent objects. The sensor has a magnetic rod, a sensor coil, and a capacitor attached to the sensor coil so as to form a tuned circuit. A first end of the rod is insertable into a first end of the coil and moveable along the axis of the coil. The rod has an end mount at its second end, as does the coil, which permits the sensor to be attached between the two objects. When the objects move, the rod moves along the coil. The interrogator having at least one interrogator coil, transmit circuitry for delivering to the sensor coil an excitation signal through a range of frequencies, and receive circuitry for receiving a response signal from the sensor coil. The change in frequency of the response signal is related to the amount of motion of the rod inside the coil.

For orthopedic applications, an advantage of the invention is that it provides a non-invasive system that incorporates an implantable passive sensor and an external interrogating device. The system is especially useful to diagnose spinal fusion postoperatively, by measuring the changes in separation of the vertebrae. The sensor response can be correlated to the relative motion of the vertebrae. The system can also be used for diagnosing other types of bone fusion, such as motion between an orthopedic implant and the surrounding bone. Small motions in this case, indicate implant loosening. The system can also measure motion between two bone segments of a fracture. Small motions in this case, indicate non-fusion of the fracture.

For spinal fusion applications, when a patient postoperatively complains of pain, the physician needs to determine whether the pain is the same as the preoperative pain or if it is from a different source. The sensor/interrogator system may be used to diagnose whether the spine has fused (a new source of pain must be the cause) or not (the same area may be causing the pain). This determination will affect the patient's treatment. In addition, as the patient is monitored postoperatively, the physician can use the information from the system to guide the patient's rehabilitation program, allowing a faster recovery time and reduced healthcare costs. In the past, methods to diagnose spinal fusion have used radiographic tools. In contrast, the system described herein does not need radiography, and allows the physician to diagnose spinal fusion in his or her office.

BRIEF DESCRIPTION OF THE DRAWINGS

FIG. 9 illustrates the relationship of the sensor frequency response, as detected by the interrogator, and the displacement of the sensor rod relative to the sensor coil.

FIG. 10 illustrates a sensor-pair configuration, which may be used as an alternative to the sensor of FIG. 1.

FIG. 11 illustrates an application of the sensor-pair of FIG. 10.

DETAILED DESCRIPTION

Single Sensor Configuration

Figure 1:
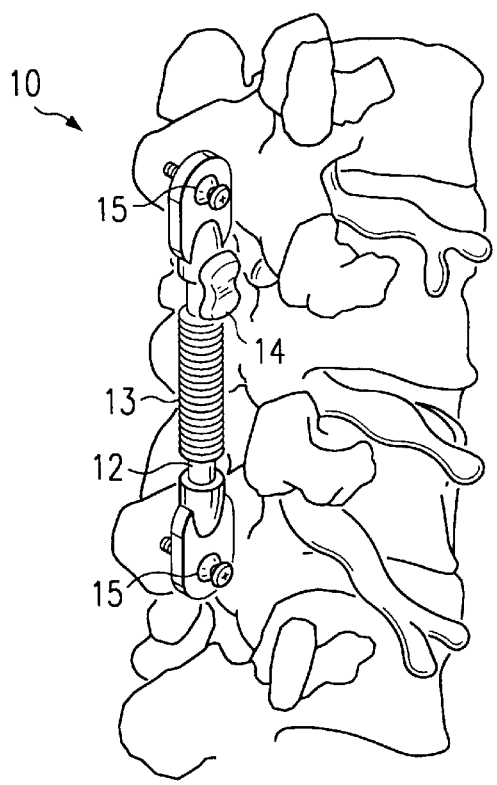
FIG. 1 illustrates a sensor in accordance with the invention, affixed between two vertebra of the human spine.

FIG. 1 illustrates a displacement sensor 10 in accordance with the invention. In the example of FIG. 1, sensor 10 is used to measure displacement along the human spine and is implanted within the lumbar spine. Sensor 10 is comprised of rod 12, coil 13, capacitor 14, and end mounts 15.

Sensor 10 is particularly useful in environments in which wires and other types of electrical leads are impractical. As explained below, to obtain a displacement measurement, an interrogator device (not shown in FIG. 1) is placed near sensor 10. In the orthopedic application of FIG. 1, where sensor 10 is implanted, the interrogator device is external to the body.

The orthopedic application of FIG. 1 is but one application of sensor 10. In general, sensor 10 could be implanted between any two objects and used to noninvasively measure the displacement between them. For example, for structural applications, sensor 10 could be placed between blocks of a bridge or building. The size and robustness of sensor 10 is easily scaled to the type of application and to the environment in which it is to be used.

Regardless of the application, the objects whose displacements are to be measured are "adjacent" in the sense that an end mount 15 of sensor 10 may be attached to each object. The only limitation is that the end mounts 15 of sensor 10 each be affixed in a manner that permits sensor 10 to "bridge" the two objects and that permits coil 13 and rod 12 to move relative to each other if the objects move. The term "objects" is used herein in the broadest sense; the two "objects" between which sensor 10 is attached could be two surfaces of two different pieces of material or two surfaces of a single piece of material.

End mounts 15 are at either end of sensor 10. Each end mount 15 is attached to one of two objects whose displacement is to be measured. In the example of FIG. 1, end mounts 15 are ball joints. Motion is measured along a single axis—that of the sensor 10. There may be more degrees of freedom, but only axial motion is sensed. Screws are used to attach the end mounts 15 to the vertebrae through holes in end mounts 15.

Figure 2:
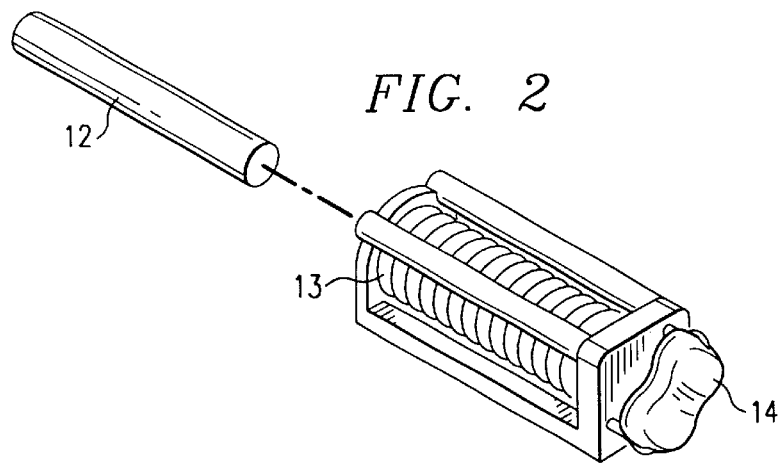
FIG. 2 illustrates a sensor similar to that shown in FIG. 1, with its rod and coil separated.
Figure 3:
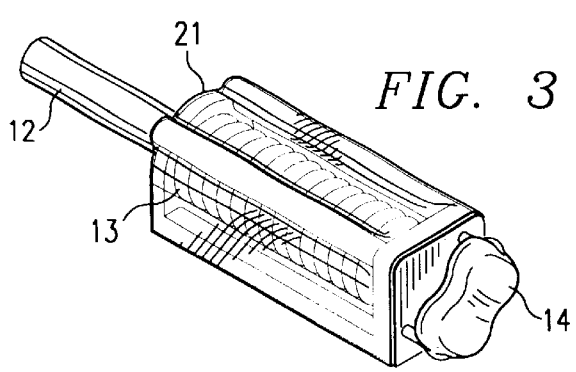
FIG. 3 illustrates the sensor of FIG. 2, with its rod inserted into the coil, and with the addition of a protective sheath.

FIGS. 2 and 3 illustrate sensor 10 with its coil 13 and rod 12 segments separated and coupled, respectively. In FIG. 2, sensor 10 is shown without end mounts. FIG. 3 further illustrates a flexible sheath 21, which may be placed over rod 12, coil 13, and capacitor 14. Sheath 21 is typically used when sensor 10 is implanted for biomedical applications, such as the orthopedic application of FIG. 1.

In operation, as explained below, the motion of rod 12 within coil 13 can be correlated to the relative motion of the two objects to which sensor 10 is attached. In the example of FIG. 1, the motion of rod 12 within coil 13 can be correlated to lumbar spine motion and therefore to spinal fusion success. Sensor 10 may be positioned between any two vertebrae involved in the spinal fusion or on the ends of a spinal fusion segment. More than one sensor 10 could be implanted. Sensor 10 can be attached to the anterior or anterolateral spine or the vertebral body. Sensor 10 can be attached to the posterior spine on either the spinous processes, transverse processes or the facets. Alternative attachment sites may be necessary given the specific anatomy of a patient. In the example of FIG. 1, sensor 10 is attached to the spinous processes.

A vast variety of attachment mechanisms can be used as end mounts 15, such as rivets, epoxy, or spring mechanisms. End mounts 15 may themselves be some type of screw or insertion post. For some applications, the attachment means should rigidly attach sensor 10 to the objects whose displacement is to be measured, minimizing any relative motion between sensor 10 and the objects to which it is attached. For other applications, end mounts 15 might be in the form of a loop or bushing that permits slight misalignment.

Rod 12 is oriented along the direction of expected motion and travels along the longitudinal axis of coil 13 as motion occurs. Rod 12 is made from a magnetically permeable material such as ferrite. The optimum rod size can be determined experimentally and depends on the application; sensor 10 is easily scaled in size for different applications. The optimum rod size may involve a tradeoff between the size of the objects whose displacement is to be measured, their expected displacement, and the distance between sensor 10 and the external interrogator device.

For orthopedic applications, rod 12 will typically range in length from one-half inch upwards, depending on where it is attached to the spine. Its diameter will usually range from one-eighth to one-quarter inch.

Coil 13 is comprised of coiled wire, the diameter of which again depends on the application and other dimensions of sensor 10. The inner diameter of coil 13 is slightly larger than the outer diameter of rod 12. For best performance, the length of coil 13 may range from three-quarters the length of rod 12 to twice as long as rod 12.

For orthopedic applications, a typical range of wire diameters is 28 AWG (American Wire Gauge) to 40 AWG. The dimensions of coil 13 might range from one-fourth to three-quarters inch long by one-eighth to three-eighths inch in internal diameter. For other applications, the dimensions of coil 13 again depend on considerations such as the environment in which sensor 10 is placed and on the expected distance from the external interrogator device.

Capacitor 14 is attached to coil 13, and is chosen to set the resonant frequency of sensor 10. A typical frequency range for various applications is 1 to 10 MHz. For this frequency range, the size of capacitor 14 might range from 50 pF to 0.01 $\mu$F.

A suitable capacitor size for spinal fusion applications has been determined experimentally as 220 to 1000 pF. However, for other applications, the capacitor size depends on considerations such as the maximum allowable size of the coil 13, desired resonant frequency of sensor 10, and the need to minimize the effects of stray capacitance on the resonant frequency.

Sensor 10 uses a tuned radio frequency circuit to achieve displacement measurement. The resonant frequency (f) is set by the value of an inductance (L) and the capacitance (C) of capacitor 14, and is given by:

$$f = \frac{1}{2\pi\sqrt{LC}}$$

The inductance is determined by the plunge depth of rod 12, which, in turn, is determined by the spacing between the two objects to which sensor 10 is attached.

Means other than a capacitor 14 external to coil 13 may be used to provide a resonant circuit. For example, the coil 13 could be made self resonant. Alternatively, it could be resonated with stripline, with a gyrator, or with a capacitor in the interrogator unit. Furthermore, although resonance improves the output signal, the concept of measuring relative displacement remotely using a variable magnetic coupling between two magnetically active objects may be implemented without resonance.

Sensor 10 is passive in that no battery or other energy source is required to power it. When excited by the interrogator device, its tuned circuit absorbs and re-radiates a signal at the sensor resonant frequency. The resonant frequency changes as the plunge depth of the rod 12 changes. This permits displacement of rod 12 within coil 13 to be inferred and used to measure displacement between the objects. For the application of FIG. 1, the spacing between vertebrae is inferred from a measurement of the resonant frequency of the tuned circuit.

For biomedical applications, such as the spinal application of FIG. 1, sensor 10 might be desired to be biocompatible. These considerations call for the use of biocompatible materials for each component, coating the components with a biocompatible material, or covering sensor 10 with a biocompatible cover to achieve biocompatibility. One of these methods, as well as any combination of these methods, can be used. The method chosen should not interfere with the ability of rod 12 to move within coil 13.

Another consideration for biomedical and other applications that call for sensor 10 to be placed in a fluid environment, is the need to prevent shorting between the elements of sensor 10. A sheath, such as sheath 21 of FIG. 3, may be desirable to prevent shorting and permit proper functioning. Sheath 21 may be fabricated as a rubber or plastic sleeve, latex tubing, or heat shrink coating. Biocompatible materials similar to those used for angioplasty could be used.

A feature of sensor 10 is that it does not interfere with normal motion of the objects to which it is attached. Specifically, for orthopedic applications, sensor 10 does not compromise the normal kinematics of the body. Sensor 10 may be attached to anatomic positions such as the spinous process or facet that will not interfere with spine motion. In addition, sensor 10 can be used with implanted fixation devices such as pedicle screw fixation systems or spinal fusion cages and can be viewed radiographically.

Interrogator

Figure 4:
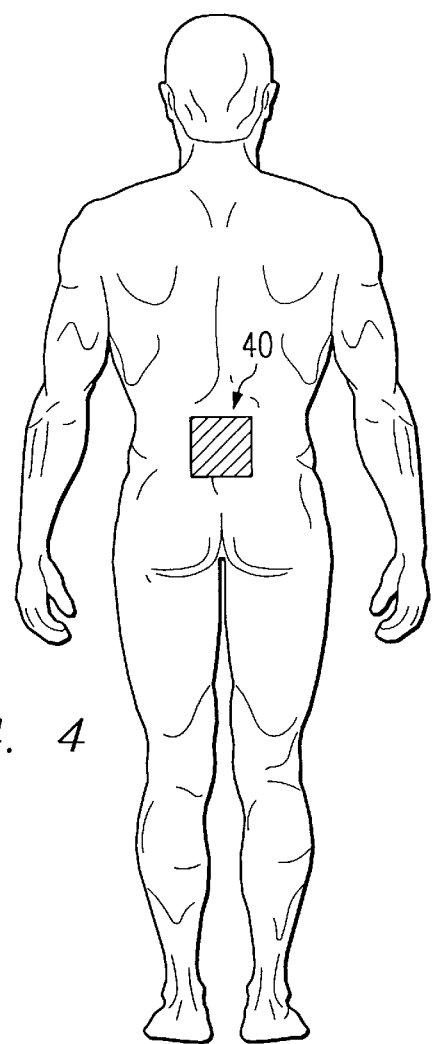
FIG. 4 illustrates the placement of an interrogator used to transmit an excitation signal to the sensor and receive a response signal from the sensor.

FIG. 4 illustrates interrogator 40, placed against a patient's back during displacement measurement. Thus, for orthopedic or other biomedical applications, sensor 10 may be internal to the body, whereas interrogator 40 is external and introduced only when measurements are desired. Thus, in general, sensor 10 is not disruptive to normal movement or operation of the environment in which it is used; interrogator 40 need only be in place when measurements are to be obtained.

During a measurement session, interrogator 40 is placed proximate to sensor 10. To obtain a displacement measurement, interrogator 40 "reads" sensor 10 using an interrogation coil or set of coils and appropriate circuitry.

The distance between interrogator 40 and sensor 10 need not remain constant in order for the system to work correctly. An increase in separation distance will result in a reduced signal, but will not affect the frequency response.

Figure 5:
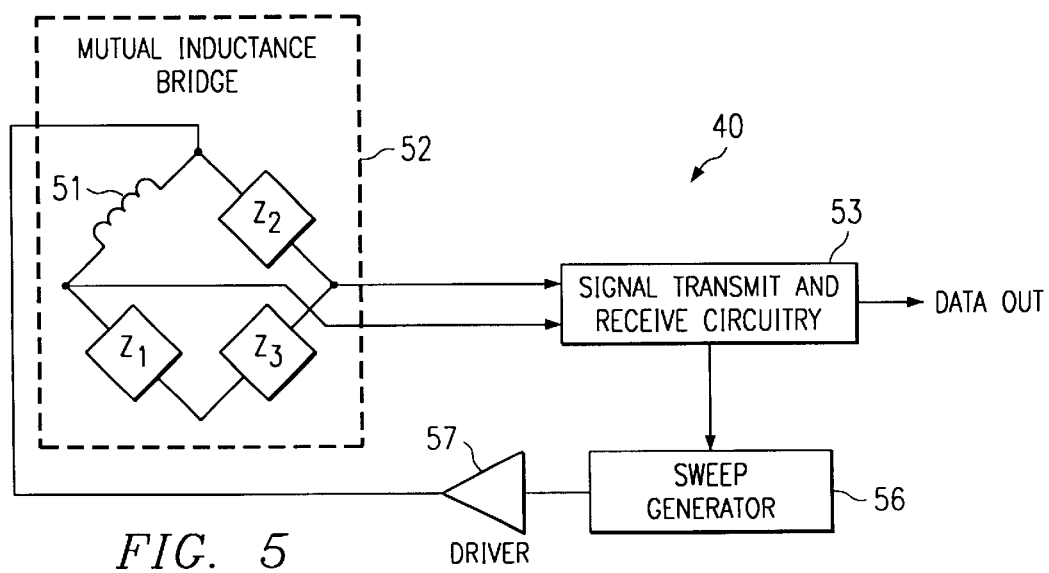
FIG. 5 illustrates one implementation of the circuitry of the interrogator of FIG. 4.

FIG. 5 is a block diagram of one example of interrogator 40. It has an interrogation coil 51, a mutual inductance bridge 52, signal transmit and receive circuitry 53, a swept frequency source 56, and a driver 57.

During a measurement session, interrogation coil 51 is placed sufficiently near sensor 10 so as to loosely couple the sensor coil 13 and interrogation coil 51. The interrogation coil 51 is driven by the swept frequency source 56 through the mutual inductance bridge 52 over a frequency span that encompasses the range of possible resonant frequencies of sensor 10. This frequency range is bounded by the frequency associated with minimum displacement and the frequency associated with maximum displacement of rod 12 relative to coil 13. As the frequency sweeps through the resonant frequency of sensor 10, sensor 10 absorbs and re-radiates energy, resulting in a change in the output of the mutual inductance bridge 52.

Figure 6:
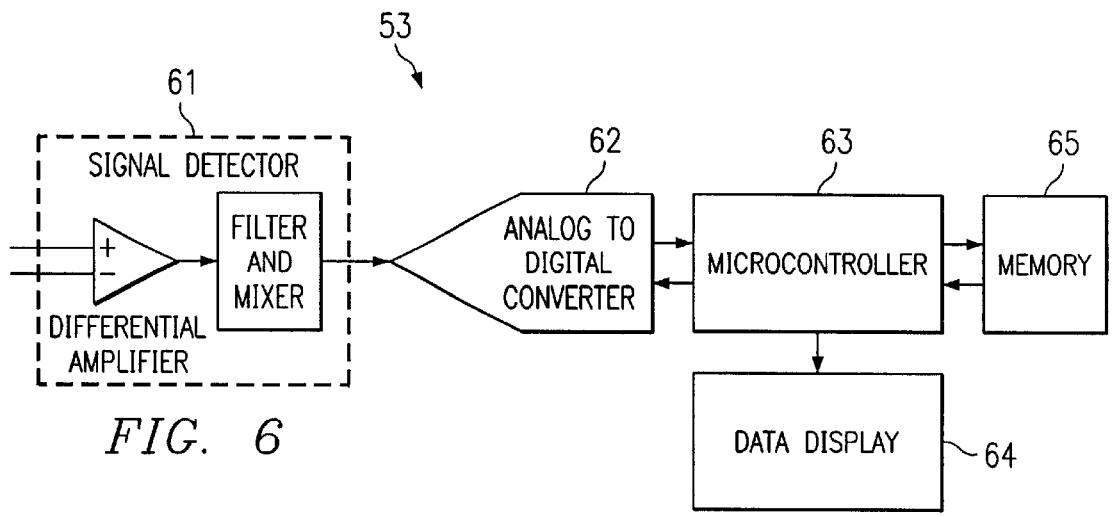
FIG. 6 illustrates an example of the signal receive circuitry of the interrogator of FIG. 5.

FIG. 6 illustrates an example of signal transmit and receive circuitry 53. It has a signal detector circuit 61, an analog to digital converter 62, a microcontroller 63, memory 65, and a data output interface 64. Its functions include control of the swept frequency source 56, calibration of the mutual inductance bridge 52, extraction of the measured data, and formatting of the user output display.

In the example of FIGS. 5 and 6, frequency source 56 is a commercially available integrated circuit, but other types of frequency generation techniques may be implemented. At the receive side of interrogator 40, the output of frequency source 56 may be mixed with the received signal for coherent detection. The amplitude of the resulting signal will then vary with frequency. This mixing technique is useful to enhance the signal to noise ratio and sensitivity of the interrogator.

In the example of FIG. 5, coil 51 is a single coil loop antenna that transmits an excitation signal to coil 13 and receives a response signal. In other embodiments, multiple coils (transmit and receive) could be used. Various AC coupling or mechanical nulling techniques can be used to minimize the offset portion of the signal. This permits increased gain of the received signal, and thereby increases the sensitivity of interrogator 40.

Figure 7:
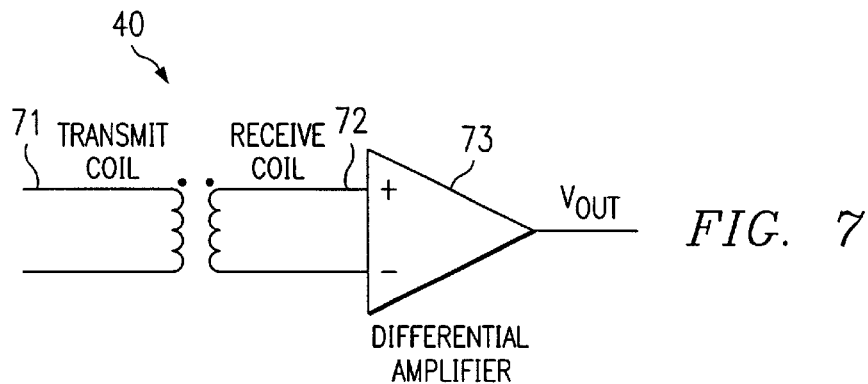
FIG. 7 illustrates a two-coil embodiment of the interrogator of FIG. 4.

FIG. 7 illustrates another example of interrogator 40. Two coils 71 and 72 are arranged in a hull coupling geometry. The coils 71 and 72 are overlapped side by side at the critical coupling spacing so that the field from the transmit coil 71 nulls that of the receive coil 72. A differential amplifier 73 receives and amplifies the output of the receive coil 72.

Figure 8:
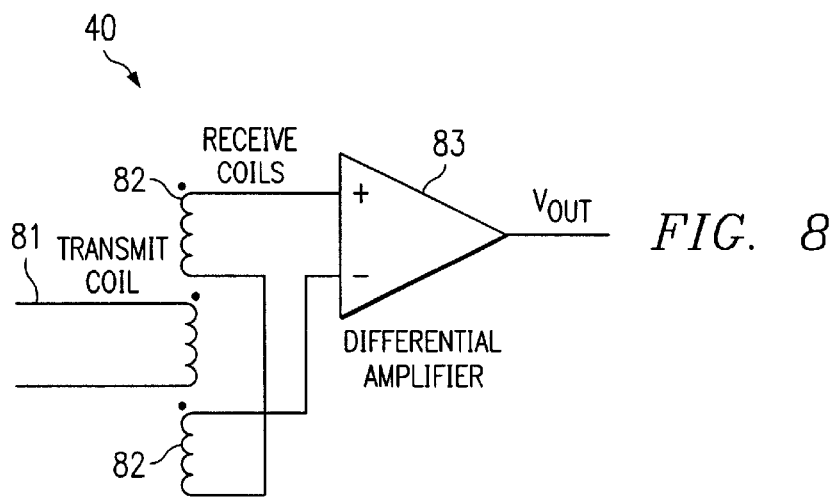
FIG. 8 illustrates a three-coil embodiment of the interrogator of FIG. 4.

FIG. 8 illustrates a three coil geometry of the interrogator 40. Coil 81 is a transmit coil. Two receive coils 82 are connected as a differential receiver and cancel the transmitted signal. A differential amplifier 83 measures the difference between the positive signal from one receive coil 82 and the equal in amplitude but opposite in phase signal from the other receive coil 82, and provides an amplified output of the difference.

For the interrogator embodiments of FIGS. 7 and 8, interrogation is accomplished by loosely coupling to sensor 10 and sweeping the frequency over the anticipated resonant frequency of the sensor. The transmit coil 71 or 81 and receive coil(s) 72 or 82 can both couple to sensor coil 13, but not to each other. As the frequency sweeps through the resonance of sensor 10, energy is coupled from the transmit coil 71 or 81 to the receive coils(s) 72 or 82 via the sensor's tuned circuit. The output of the receive coil(s) 72 or 82 is detected and processed as before.

FIG. 9 illustrates the relationship between the frequency response of sensor 10, as detected by interrogator 40, and the relative displacement of rod 12 relative to coil 13. This graph shows that displacements of approximately 0.1 mm can be resolved.

Sensor Pair Configuration

FIG. 10 illustrates an alternative sensor configuration, comprised of a pair of sensors 100. Each sensor 100 has a rod 102, a coil 103, and a capacitor 104. Like sensor 10, the rod 102, coil 103, and capacitor 104 form a tuned circuit. However, unlike the rods of sensors 10, the rod 102 of a sensor 100 does not move relative to its coil 13. It is the displacement between sensors 100 that is of interest.

Sensors 100 are used to measure the displacement between any two locations. One sensor 100 is attached or embedded at one location, and the other sensor 100 to a nearby location.

One advantage of the configuration of FIG. 10 is that the sensors 100 can be mounted independently, with no physical connection between the two. However, the sensors 100 should be initially placed sufficiently close together and in the correct orientation so as to form the overcoupled system described below. In general, the sensors 100 are placed substantially parallel to each other and offset axially.

Like sensor 10, sensors 100 may each have end mounts (not shown). Furthermore, an end mount might be at only one end rather than at both ends. However, an advantage of the configuration of FIG. 10 is that sensors 100 may be simply embedded within an object or within each of two different objects; there is no need for mechanical coupling of sensors 100.

For the sensor embodiment of FIG. 10, two tuned circuits are used, both to the same resonant frequency. Sensors 100 have a fixed frequency response. When placed in proximity to one another, the tuned circuits of sensors 100 interact and form an overcoupled resonant system. Rather than a single resonant peak, there is a double peak. The frequency separation between the peaks is sensitive to the spacing between the two sensors 100. Relative motion between the sensors 100 is detectable by a shift in peak separation.

FIG. 11 illustrates the application of sensors 100 for measuring spinal fusion. Rods 102 are threaded on the end to allow them to be screwed directly into the spine. If a large area of the spine is of interest, numerous sensors 100 could be implanted. The relative motion of sensors 100 can be correlated to spine motion and therefore spinal fusion success.

The sensor-pair configuration of FIGS. 10 and 11 can be interrogated with an interrogator that is similar to interrogator 40. The primary difference is that the data is inferred from the frequency separation of a double peak response instead of the location of a single resonant peak.

Orthopedic Applications

In practice, for orthopedic applications, one or more sensors 10 are implanted during surgery. The length of rod 12 is chosen so that at rest, rod 12 is positioned within coil 13 only one-quarter to three-quarters the length of rod 12. For the sensor-pair configuration of FIG. 10, the two sensors 100 are placed parallel to each other and offset axially.

When the patient visits the physician, the interrogator 40 is secured to the patient. It is placed sufficiently close to the patient such that the distance between the sensor 10 (or sensors 100) and the interrogator 40 is minimized. As the patient moves, the internal sensor 101 frequency response changes will be measured and correlated to motion.

For the spinal fusion application of FIG. 1, theoretically, if the spinal fusion surgery was successful, there should be no measurable motion between the spinal fusion segments. The changes in the sensor response can then be correlated to relative motion of the vertebrae and to spinal fusion success. Unlike flexion-extension x-rays and CT scans which measure a static position and compare it to another static position, sensor 10 and interrogator 60 can dynamically measure motion and any sensor response changes can be correlated to fusion success. Dynamic measurement and analysis of motions are completed through automated data analysis, allowing the physician to see the outcome of the diagnostic test immediately after the test is completed. Therefore, the spinal fusion healing progression could also be objectively observed over time.

The same system can be used for diagnosing other types of bone fusion. For instance, the system can measure motion between an orthopedic implant and the surrounding bone. Small motions in this case would indicate implant loosening. The system can also measure motion between two bone segments of a fracture. Small motions in this case would indicate a non-fusion of the fracture. Therefore, the invention provides a very simple and consistent measuring system for diagnosing small motions between bones or between orthopedic implants and bone surfaces without being invasive. In general, the sensors are attached to "skeletal objects" whether they be natural or artificial.

Other Embodiments

Although the present invention has been described in detail, it should be understood that various changes, substitutions, and alterations can be made hereto without departing from the spirit and scope of the invention as defined by the appended claims.

What is claimed is:

1. A system for performing a remote measurement of the displacement between two adjacent objects, comprising
   a sensor for attachment between the objects, the sensor having a magnetic rod, the rod having a first end and a second end, and a sensor coil, the sensor coil having the shape of a hollow cylinder having a first end and a second end and having a longitudinal axis between the first end and the second end;
   wherein the first end of the rod is insertable into the first end of the sensor coil and moveable along the longitudinal axis of the sensor coil;
   wherein the rod has an end mount at the second end of the rod, the end mount operable to be attached to one of the objects, and
   wherein the sensor coil has an end mount at the second end of the sensor coil, the end mount operable to be attached to the other of the objects, and
   an interrogator having a transmit coil and at least one receive coil, transmit circuitry for delivering to the sensor coil an excitation signal through a range of frequencies, and receive circuitry for receiving a response signal from the sensor coil;
   wherein the transmit coil and the at least one receive coil are configured in a nulling geometry.

2. The system of claim 1, wherein the nulling geometry has one receiver coil and one transmitter coil.

3. The system of claim 2, wherein the nulling geometry has two receiver coils and one transmitter coil.

4. The system of claim 1, further comprising a flexible sheath enclosing the sensor.

5. The system of claim 1, wherein the sensor is coated with a biocompatible material.

6. The system of claim 1, wherein the sensor is made from biocompatible materials.

7. The system of claim 1, wherein the interrogator further has mixer circuitry for mixing the transmitted signal and the received signal.

8. The system of claim 1, wherein the interrogator has digital processing circuitry for processing the received signal.

9. The system of claim 1, wherein the interrogator has a mutual inductance bridge electrically connected to at least one coil.

10. The system of claim 1, further comprising means for adjusting the resonance of the sensor.

11. A method for determining displacement between two objects, comprising the steps of:
    attaching a first end of a magnetic rod to a first object;
    attaching a first end of a sensor coil to a second object;
    wherein the attaching steps are performed such that the rod is partially inserted into the coil and the rod and coil extend between the objects, thereby forming a sensor;
    interrogating the sensor with an interrogation signal; and
    receiving a response signal from the sensor, said response signal having a frequency that indicates motion of the rod within the sensor coil;
    wherein the receiving step is performed with at least one receive coil and at least one transmit coil configured in a nulling geometry.

12. The method of claim 11, wherein the nulling geometry has one transmit coil and one receive coil.

13. The method of claim 12, wherein the nulling geometry has two receive coils and one transmit coil.

14. The method of claim 13, wherein the two receive coils receive a signal equal in amplitude and opposite in phase.

15. The method of claim 11, further comprising the step of encasing the sensor in a protective sheath.

16. The method of claim 11, further comprising the step of creating an electrical resonance of the sensor.

17. The method of claim 11, wherein the sensor is self resonating in response to the interrogation step.

18. A method for determining displacement between two objects within a living body, comprising the steps of:

attaching a first end of a magnetic rod to a first skeletal object;

attaching a first end of a sensor coil to a second skeletal object;

wherein the attaching steps are performed such that the rod is partially inserted into the coil and the rod and coil extend between the objects, thereby forming a sensor;

interrogating the sensor with an interrogation signal;

receiving a response signal from the sensor, said response signal having a frequency that indicates motion of the rod within the sensor coil;

wherein the receiving step is performed with at least one receive coil and at least one transmit coil configured in a nulling geometry.

19. The method of claim 18, wherein the skeletal objects are portions of the spine.

20. The method of claim 18, further comprising the step of creating an electrical resonance of the sensor.

21. The method of claim 18, wherein the nulling geometry has one transmit coil and one receive coil.

22. The method of claim 18, wherein the nulling geometry has two receive coils and one transmit coil.

23. The method of claim 22, wherein the two receive coils receive a signal equal in amplitude and opposite in phase.

24. The method of claim 18, wherein the sensor is self resonating in response to the interrogation step.

* * * * *